US008409077B2

(12) United States Patent
Orihara et al.

(10) Patent No.: US 8,409,077 B2
(45) Date of Patent: Apr. 2, 2013

(54) CAPSULE ENDOSCOPE (75) Inventors: Tatsuya Orihara, Shibuya (JP); Hitoshi Fukuhori, Shibuya (JP)

(73) Assignee: Olympus Medical Systems Corp., Tokyo (JP)

( * ) Notice: Subject to any disclaimer, the term of this patent is extended or adjusted under 35 U.S.C. 154(b) by 1317 days.

(21) Appl. No.: 12/215,156

(22) Filed: Jun. 24, 2008

(65) Prior Publication Data

US 2009/0062605 A1    Mar. 5, 2009

(30) Foreign Application Priority Data

Aug. 31, 2007 (JP) .................................. 2007-225034

(51) Int. Cl.
*A61B 1/04* (2006.01)
(52) U.S. Cl. ........................................................ 600/109
(58) Field of Classification Search .................. 600/103, 600/109, 117–118, 160
See application file for complete search history.

(56) References Cited

U.S. PATENT DOCUMENTS

| 2005/0177069 | A1* | 8/2005 | Takizawa et al. | 600/573 |
| 2006/0069312 | A1 | 3/2006 | O'Connor | |
| 2006/0246218 | A1* | 11/2006 | Bienkiewicz et al. | 427/249.1 |
| 2007/0282164 | A1* | 12/2007 | Frisch et al. | 600/109 |
| 2008/0002146 | A1* | 1/2008 | Stachowski et al. | 351/160 H |
| 2009/0018396 | A1* | 1/2009 | Takizawa et al. | 600/127 |

FOREIGN PATENT DOCUMENTS

| JP | 10-057300 | 3/1998 |
| JP | 2002-112961 | 4/2002 |
| JP | 2003-207601 | 7/2003 |
| JP | 2005-152043 | 6/2005 |
| JP | 2005-192820 | 7/2005 |
| JP | 2005-312809 | 11/2005 |
| JP | 2006-000282 | 1/2006 |
| JP | 2007-000177 | 1/2007 |
| JP | 2007-014634 | 1/2007 |
| JP | 2007-075248 | 3/2007 |
| JP | 2007-159642 | 6/2007 |
| WO | WO 2007/034712 | 3/2007 |

* cited by examiner

*Primary Examiner* — Philip R Smith
(74) *Attorney, Agent, or Firm* — Kenyon & Kenyon LLP (57) ABSTRACT A capsule endoscope can prevent any fall of the efficiency of observation by reducing the substance or substances adhering to the outer surface of the front end cover such as food residue and mucus. The capsule endoscope includes a dome-shaped front end cover provided on the outer surface with photocatalytic coating, an image pickup means arranged in the front end cover to pick up images of the inside of an object of examination into which the endoscope is introduced and acquire image information on the inside of the object of examination and a lighting section arranged around the image pickup means within the dome-shaped front end cover.

6 Claims, 11 Drawing Sheets

FIG.8 emission spectrum of white LED

FIG.9 emission spectrum of ultraviolet LEDs

FIG.10A emission timing of ultraviolet LED

FIG.10B emission timing of white LEDs

FIG.10C image acquisition timing of image pickup means

FIG.11 example of using white LED with relatively high intensity at short wavelength of 400 nm and its vicinity capable of exciting photocatalyst

FIG.12 example of arranging ultraviolet LED near object unit

CAPSULE ENDOSCOPE

CROSS REFERENCE TO RELATED APPLICATION

This application is based upon and claims the benefit of priority from the prior Japanese Patent Application No. 2007-225034, filed on Aug. 31, 2007, the entire contents of which including the specification, the drawings and the abstract are incorporated herein by reference.

BACKGROUND OF THE INVENTION

1. Field of the Invention

This invention relates to a capsule endoscope adapted to be introduced into an object of examination and equipped with various function executing means for executing predetermined functions in order to collect information from the inside of the object of examination and a substrate bearing such function executing means. A capsule endoscope according to the present invention may typically be of a swallowable type.

2. Description of the Related Art

Capsule endoscopes that are equipped with an image pickup function and a wireless communication function have become available in the field of endoscope in recent years. A capsule endoscope that is swallowed by a subject, or an object of examination, for observation (physical examination) is then driven to move through the inside of the stomach, the small intestine and other organs (the body cavity) as the organs peristaltically wave until it is naturally excreted from the living body of the subject so as to pick up images of the inside of the body by means of its image pickup function during the period of observation. The image data of the images picked up in the body cavity by the capsule endoscope during the period of observation are sequentially transmitted to an external unit arranged outside the object of examination by means of the wireless communication function such as Bluetooth and accumulated in the memory of the external unit. As the subject carries the external unit having a wireless communication function and a memory function with him or her, he or she, whoever appropriate, can move without restrictions during the period of observation from the time of swallowing the capsule endoscope to the time of excreting it. After the observation, the images picked up from the body cavity can be displayed on a display screen by a doctor or a nurse for diagnosis according to the image data accumulated in the memory of the external unit.

Known capsule endoscopes include those of a swallowable type as disclosed in Patent Document 1 (JP 2007-14634-A) that are also equipped with the above listed functions. Such a capsule endoscope includes a lighting member (a light emitting diode to be referred to as LED hereinafter), an image sensor, drive circuits for them, a power supply section including a battery and a transmission section for transmitting image data from the image sensor to an external unit, which are arranged on respective arrangement substrates as so many IC. The substrates are then connected to each other by way of a strip substrate, and all the components are contained in a hermitically sealed and capsule-shaped container having dome-shaped opposite ends.

The above-cited Patent Document 1 that discloses a an indwelling device for capsule type medial apparatus also describes that the holding section thereof is partly provided with anti-stain coating such as hydrophilic coating typically of a photocatalyst in order to minimize the influence of the apparatus on observation. Such hydrophilic coating of a photocatalyst has been and being finding applications in various fields. For example, Patent Document 2 (JP 2003-207601-A) proposes an objective lens to be used for an optical pickup of an optical disk device. The surface of the objective lens is coated with a hydrophilic photocatalytic material that is excited by light having a wavelength not greater than 420 nm. The photocatalytic material becomes so hydrophilic that it produces a contact angle with water substantially equal to 0° when excited with light having a wavelength not greater than 420 nm. Then, if moisture adheres to the surface of the lens, it does not form any fine droplets but becomes a thin water film on the surface. Thus, the objective lens is hardly clouded if the environment changes.

Patent Document 3 (JP 2005-312809-A) describes a technique of forming a thin film containing a photocatalyst on the outer surface of a light transmitting member arranged at the front end of an optical member of the part of an endoscope, a medical endoscope in particular which may typically be a hard mirror or a soft mirror, to be inserted into the body cavity of a subject for the purpose of observing and treating the inside of the subject.

SUMMARY OF THE INVENTION

When a capsule endoscope as described above is inserted into the body cavity of a subject for the purpose of observing the inside of the subject, the food residue or the mucus in the inside of the body cavity can partly adhere to the outer surface of the dome shaped transparent front end cover to block the observation. Therefore, it is important to reduce the adhesion of any food residue or mucus to the outer surface of the front end cover in order to prevent any fall of the efficiency of observation and improve the screening effect. However, while the retaining member of an apparatus described in the above-cited Patent Document 1 is provided partly with anti-strain coating, any substances that can adhere to the outer surface of the front end cover are not taken into consideration so that they can give rise to a problem.

While a number of coating techniques using a photocatalytic material have been disclosed, no proposal has been made to date about how such a technique can be applied to a capsule endoscope.

In view of the above-identified problems, the present invention provides a capsule endoscope including: a dome-shaped front end cover provided on the outer surface with a hydrophilic coat; an image pickup means arranged in the front end cover to pick up images of the inside of an object of examination into which the endoscope is introduced and acquire image information on the inside of the object of examination; and a lighting section arranged around the image pickup means within the dome-shaped front end cover.

Preferably, in a capsule endoscope as defined above, the viewing angle of the image pickup means is not less than 90° and the hydrophilic coat is photocatalytic coating.

Preferably, in a capsule endoscope as defined above, the lighting section is formed by using white LEDs.

Preferably, in a capsule endoscope as defined above, the lighting section is formed by using white LEDs and an ultraviolet LED.

Preferably, in a capsule endoscope as defined above, the timing of emission of light of the white LEDs and the timing of emission of light of the ultraviolet LED are differentiated from each other.

Preferably, in a capsule endoscope as defined above, the hydrophilic coat is arranged on the undulations formed on the outer surface of the front end cover.

Preferably, in a capsule endoscope as defined above, the hardness of the material of the hydrophilic coat is higher than the hardness of the material of the front end cover.

Preferably, in a capsule endoscope as defined above, the hydrophilic coat is arranged after arranging a layer of coat film of a material having a refractive index different from the refractive index of the material of the hydrophilic coat on the outer surface of the front end cover.

In another aspect of the present invention, there is provided a capsule endoscope including: a dome-shaped front end cover processed for hydrophilicity by irradiating plasma or electron beams onto the outer surface thereof; an image pickup means arranged in the front end cover to pick up images of the inside of an object of examination into which the endoscope is introduced and acquire image information on the inside of the object of examination; and a lighting section arranged around the image pickup means within the dome-shaped front end cover.

Thus, a capsule endoscope according to the present invention can pick up images of the inside of the body cavity of a subject by the image pickup means and prevent any fall of the efficiency of observation by reducing the substance or substances adhering to the outer surface of the front end cover such as food residue and mucus.

DETAILED DESCRIPTION OF THE PREFERRED EMBODIMENTS

Now, the present invention will be described in greater detail by referring to the accompanying drawings that illustrate preferred embodiments of the invention. However, it should be noted here that the present invention is by no means limited to the embodiments, which may be modified and altered in various different ways without departing from the spirit and scope of the present invention.

Figure 1:
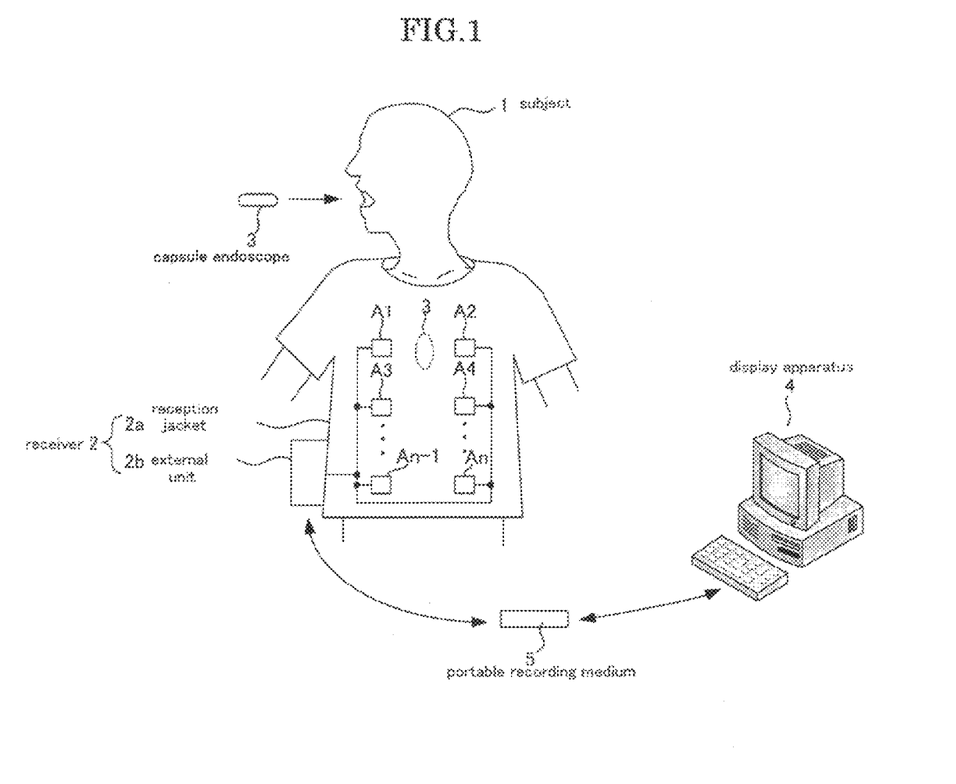
FIG. 1 is a schematic illustration of a wireless type intra-subject information acquisition system including a capsule endoscope according to the present invention, showing the overall configuration thereof.

FIG. 1 is a schematic illustration of a wireless type intra-subject information acquisition system including a capsule endoscope according to the present invention, showing the overall configuration thereof. The capsule endoscope 3 of this wireless type intra-subject information acquisition system is adapted to be introduced into the body cavity of the subject, which is a human being, through his or her mouth and pick up images of the site or sites of examination in the body cavity. Referring to FIG. 1, the wireless type intra-subject information acquisition system comprises a receiver 2 having a radio signal receiving function and a capsule endoscope 3 to be introduced into the subject 1 in order to pick up images in the body cavity and transmit data such as image signals to the receiver 2. The wireless type intra-subject information acquisition system additionally comprises a display apparatus 4 for displaying images picked up in the body cavity according to the image signals received by the receiver 2 and a portable recording medium 5 by means of which the receiver 2 and the display apparatus 4 exchange data with each other.

The receiver 2 includes a reception jacket 2a to be worn by the subject 1 and an external unit 2b for processing the radio signals received by the receiver 2, both of which are to be securely fitted to the waist of the subject 1 by means of a belt (not shown) and carried by the subject 1. In other words, the receiver 2 has a function of receiving image data acquired in the body cavity and transmitted wirelessly from the capsule endoscope 3 and the reception jacket 2a is equipped with reception antennas A1 through An and made to show a profile adapted to be worn by the subject 1, while the external unit 2b processes the radio signals received by way of the reception antennas A1 through An of the reception jacket 2a.

The display apparatus 4 displays images picked up in the body cavity by means of the capsule endoscope 3. It is configured so as to operate as a work station for displaying images according to the data acquired by the portable type recording medium 5. More specifically, the display apparatus 4 may be so designed as to directly display images by means of a CT display or a liquid crystal display or output images to some other medium such as a printer.

The portable recording medium 5 can be removably fitted to the external unit 2b and also to the display apparatus 4 and is structurally so adapted that it can record or output information when it is fitted to the external unit 2b or the display apparatus 4, whichever appropriate. More specifically, the portable recording medium 5 is fitted to the external unit 2b to record the data transmitted from the capsule type endoscope 3 while the capsule type endoscope 3 is moving in the body cavity of the subject 1, whereas it is removed from the external unit 2b and fitted to the display apparatus 4 so that the data recorded in the portable recording medium 5 are read out by the display apparatus 4 after the capsule type endoscope 3 is discharged from the subject 1. As the external unit 2b and the display apparatus 4 exchange data by way of the portable recording medium 5, which may typically be formed by using a CompactFlash (trademark) memory, the subject 1 can move freely while the capsule type endoscope 3 is picking up images in the body cavity of the subject 1 if compared with an arrangement where the external unit 2b and the display apparatus 4 are connected by way of wire. While the portable recording medium 5 is employed for data exchanges between the external apparatus 2b and the display apparatus 4 in this embodiment, the present invention is by no means limited thereto and it may alternatively be so arranged that the external unit 2b contains a recording apparatus such as a hard disk and is connected to the display apparatus 4 by way of wire or wirelessly to exchange data with the display apparatus 4.

Figure 2:
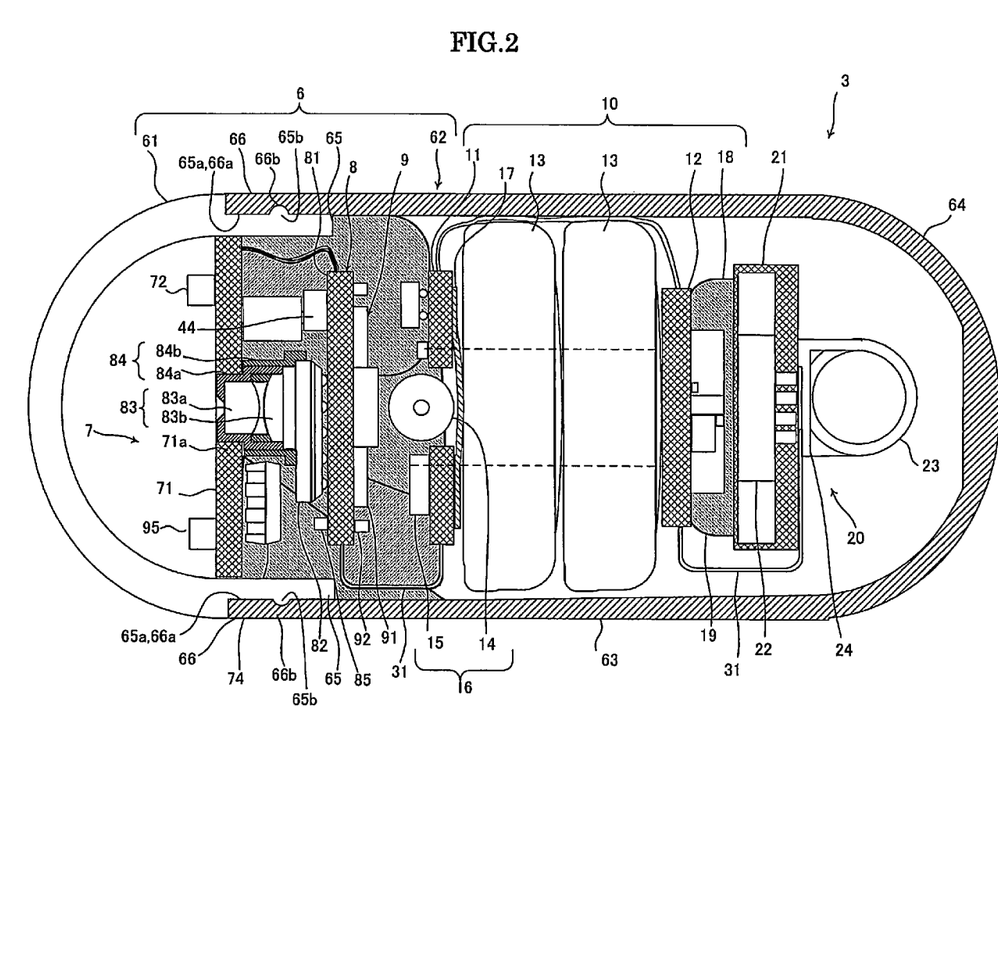
FIG. 2 is a schematic cross-sectional lateral view of a capsule endoscope according to the present invention, showing the configuration thereof.
Figure 3:
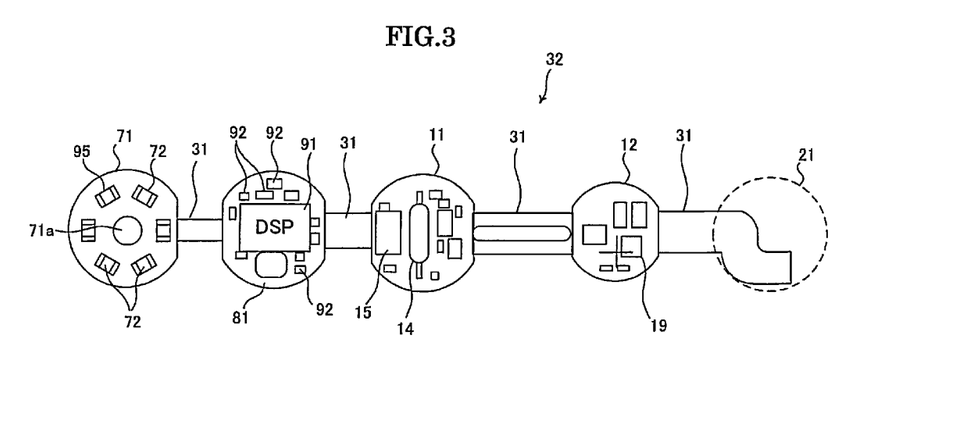
FIG. 3 is a schematic developed plan view of the rigid-flex wiring board of FIG. 1.
Figure 4:
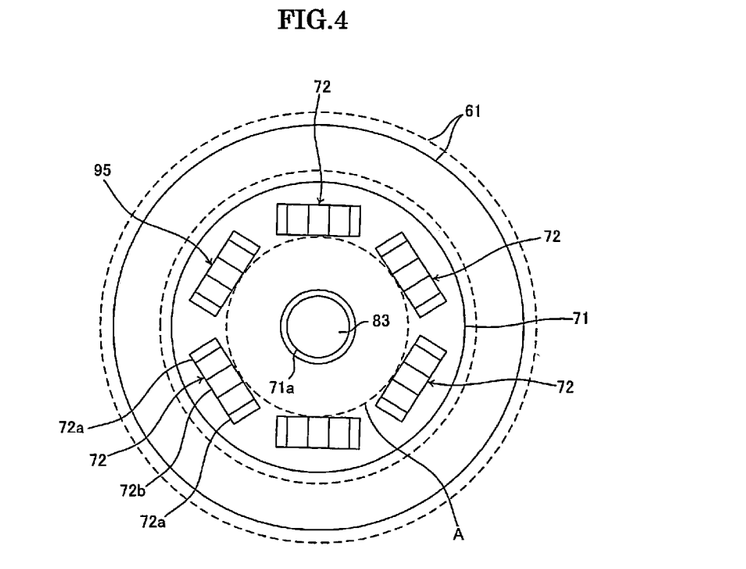
FIG. 4 is a schematic cross-sectional view of the lighting substrate of the Embodiment of FIG. 1 as viewed from the front side thereof.
Figure 5:
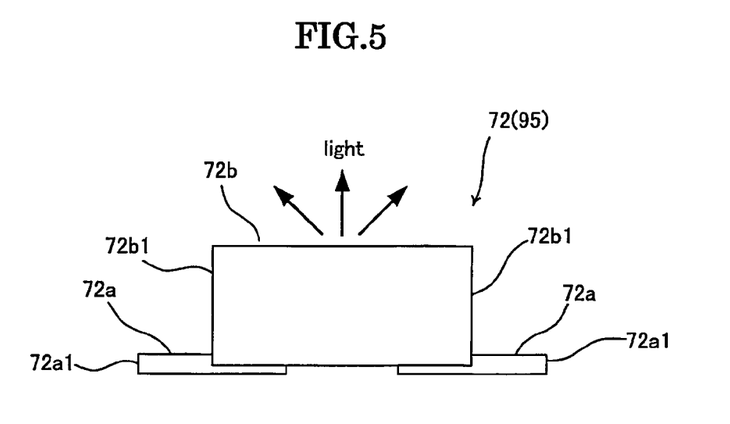
FIG. 5 is a schematic lateral view of the white LEDs of FIG. 3.
Figure 6:
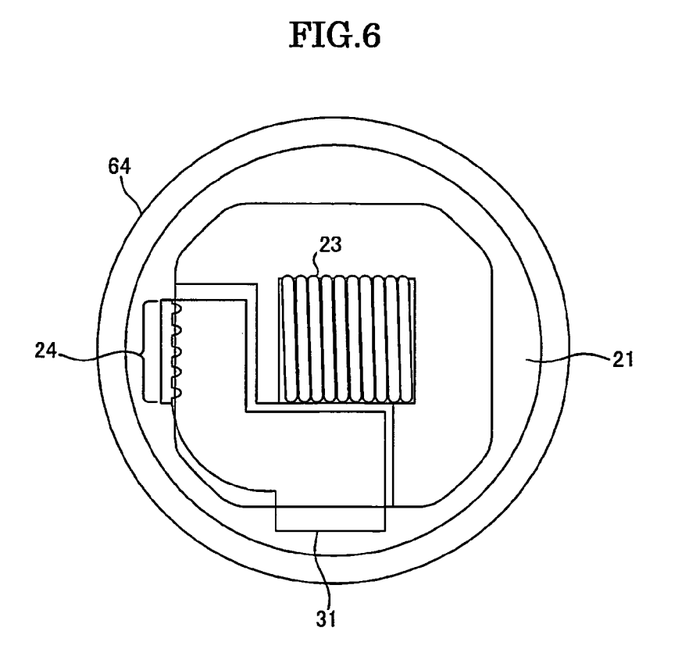
FIG. 6 is a schematic cross-sectional view of the transmission substrate of FIG. 1 as viewed from the rear side thereof.
Figure 7:
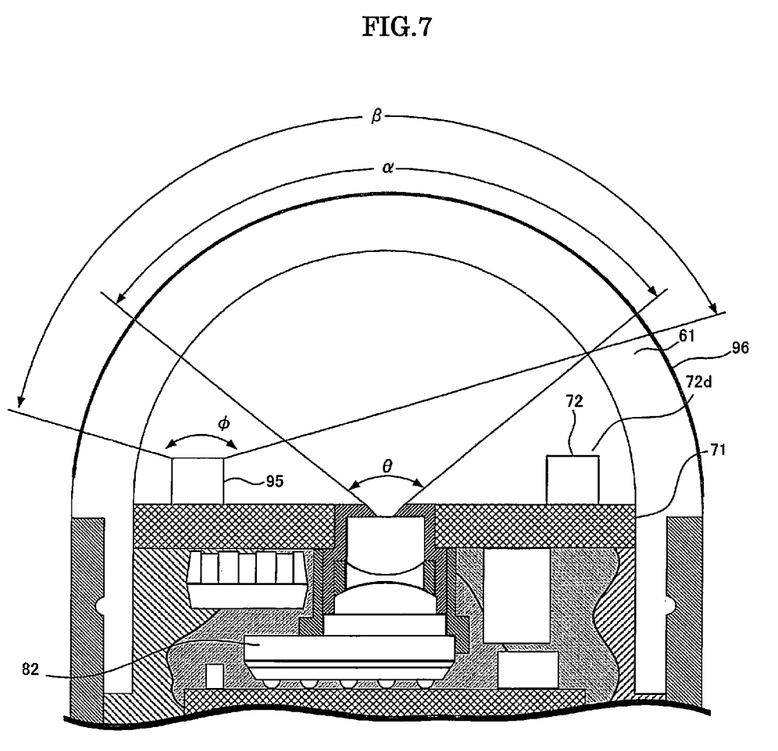
FIG. 7 is a schematic cross-sectional lateral view of the front end cover and its vicinity of the capsule endoscope of FIG. 2.

FIG. 2 is a schematic cross-sectional lateral view of a capsule endoscope 3 according to the present invention, showing the configuration thereof. FIG. 3 is a schematic developed plan view of the rigid-flex wiring board of FIG. 2 and FIG. 4 is a schematic cross-sectional view of the lighting substrate of FIG. 2 as viewed from the front side thereof (from the front end cover side in FIG. 2), while FIG. 5 is a schematic cross-sectional view of the transmission substrate of FIG. 2 as viewed from the rear side thereof (from the rear end side in FIG. 2) and FIG. 6 is a schematic cross-sectional view of the transmission substrate of FIG. 1 as viewed from the rear side thereof. FIG. 7 is a schematic cross-sectional lateral view of the front end cover and its vicinity of the capsule endoscope of FIG. 2.

As seen from FIG. 2, the capsule endoscope 3 includes a hermetically sealed container 6 that is an armor case profiled as capsule, a lighting means 7 for emitting light to illuminate a predetermined site of examination in the body cavity as a function execution means for executing a predefined function, an image pickup means 8 for receiving light reflected as a result of illuminating the predetermined site and picking up an image of the site of examination also as a function execution means, a control means 9 for controlling the operation of driving the lighting means 7 and that of driving the image pickup means 8 and processing signals, a power accumulation means 10 for accumulating electric power for driving the function execution means and a wireless transmission means 20 for wirelessly transmitting the image data acquired by the image pickup means 8 to the outside of the subject as a function execution means.

The hermetically sealed container 6 has such a size that man can swallow it without difficulty. It is formed by elastically engaging a substantially semispherical front end cover 61 and a cylindrical trunk cover 62 with each other. The lighting substrate 71, image pickup substrate 81, switch substrate 11, power supply substrate 12 and the transmission substrate 21 that are arrangement substrates are inserted into the cylindrical trunk cover 62 having a substantially semispherical bottom section at the rear end thereof and a circular opening at the front end thereof. The front end cover 61 has a semispherical dome-shaped profile and has a circular opening at the rear end of the dome. The front end cover 61 is made of a transparent material that allows light to pass through it. It is preferably molded by using cycloolefin polymer (Zeonex: trademark or the like) or polycarbonate to secure a desired optical performance and a desired strength so that light emitted from the lighting means 7 can be transmitted to the outside of the hermetically sealed container 6 while light reflected from the subject can be transmitted to the inside of the hermetically sealed container 6.

The front end cover 61 is provided on the outer surface thereof with a hydrophilic coat as shown in FIG. 7. Thus, as a result, a capsule endoscope according to the present invention provides an advantage that it reduces any food residue and/or mucus that can adhere to the front end cover 61 and prevents any fall of the efficiency of observation from taking place.

The hydrophilic coat arranged on the outer surface of the front end cover 61 can also provide an advantage that the food residue and/or the mucus adhering to the front end cover 61 to fall the efficiency of observation of the capsule endoscope 3 can be washed away with water particularly when they are remarkable.

For the purpose of the present invention, any means can be employed to provide the outer surface of the front end cover 61 with hydrophilicity. For instance, the outer surface of the front end cover 61 can be provided with hydrophilicity by subjecting it to a plasma process or a process of irradiating it with electrons instead of coating it in order to make it hydrophilic. The composition of the material can be altered and/or micro undulations of the order of several nanometers can be formed on the surface when the outer surface of the front end cover 61 is subjected to a plasma process or a process of irradiating it with electrons. Then, as a result, the hydrophilicity of the outer surface of the front end cover 61 can be improved.

Note, however, that a hydrophilic coat of a photocatalyst is used for the purpose of hydrophilic coating in the embodiments of the present invention that will be described hereinafter. FIG. 7 schematically illustrates such a hydrophilic coat of a photocatalyst (photocatalytic coating 96).

Meanwhile, when a hydrophilic coat of a photocatalyst is employed, the effect of the hydrophilic coat is poorly retained. In other words, it is difficult to retain the effect of the hydrophilic coat for a long time in body fluid. However, the coating can be held to an excited state by using a light emitting device (an LED of a material such as GaN) that emits ultraviolet rays showing a peak of spectrum at a short wavelength at part of the light emitting device of the capsule endoscope when a hydrophilic coat of a photocatalyst is employed as coating on the outer surface of the front end cover 61. Thus, such an LED is adopted in this embodiment. As the coating is excited by the LED, the function of the hydrophilic coat can be maintained for a long time regardless of the environment of operation. Thus, this embodiment provides the advantage that it reduces any food residue and/or mucus that can adhere to the front end cover 61 and prevents any fall of the efficiency of observation from taking place for a long period of time in body fluid.

A photocatalyst as described above absorbs light of energy that corresponds to a band gap and produces pairs of a hole in a valence band and an electron in a conduction band so that holes and electrons move without giving rise to any recombination and interact with substrates and adsorbed species to promote a photocatalytic reaction.

Titanium oxide ($TiO_2$) is most preferable for the photocatalyst to be employed in the photocatalytic coating 96 for the purpose of the present invention. Titanium oxide is a substance that is harmless to the human body and chemically stable. It is additionally a substance that is commercially available at low cost. Since titanium oxide does not absorb visible light, it neither alter the color of the picked up image nor degrade the image quality of the image otherwise when used as coating on the outer surface of the front end cover 61.

However, substances other than titanium oxide ($TiO_2$) can be utilized for the photocatalytic coating 96 according to the present invention. More specifically, the material of the photocatalytic coating 96 may be a substance selected from a group of substances including titanium oxide, zinc oxide, niobium oxide, tungsten oxide and zirconium oxide.

The thickness of the photocatalytic coating 96 is preferably not greater than 0.2 μm when the front end cover 61 is a transparent member in order to prevent the front end cover 61 from being colored by interference of light.

When the photocatalytic coating 96 is made of a substance selected from titanium oxide, zinc oxide, niobium oxide, tungsten oxide and zirconium oxide, the hardness of the photocatalytic coating 96 is higher than that of the front end cover 61 that is made of cycloolefin polymer (Zeonex: trademark or the like) or polycarbonate so that the photocatalytic coating 96 can reliably take the role of protecting the front end cover 61 against scars. Since the front end cover 61 can hardly be damaged as it is protected by the photocatalytic coating 96, the front end cover 61 can be handled with ease on the manufacturing line of capsule endoscopes 96 in the manufacturing plant. The net result will be a higher assembling efficiency and a higher manufacturing yield.

Micro undulations of the order of several nanometers are preferably formed on the outer surface when forming a photocatalytic coating 96 on the outer surface of the front end cover 61. The photocatalytic coating 96 can hardly be peeled off when such micro undulations are formed on the outer surface of the front end cover 61.

The trunk cover 62 is a member arranged at the back of the front end cover 61 to cover the above described function execution means. To produce the trunk cover 62, a cylindrical trunk section 63 is integrally formed with a substantially semispherical dome-shaped rear end section 64. The trunk section 63 has a circular opening at the front end thereof. The trunk cover 62 is preferably made of polysulfon in order to secure a desired level of strength. It is adapted to contain the lighting means 7, the image pickup means 8, the control means 9 and the power accumulation means 10 in the trunk section 63 thereof and the wireless transmission means 20 in the rear end section 64 thereof.

The front end cover 61 is provided at the opening thereof with a cylindrical connection terminal section 65 extending along the edge of the opening. The trunk section 63 is provided at the opening thereof with a cylindrical connection terminal section 66 extending along the edge of the opening. The connection terminal sections 65, 66 respectively have connection surfaces 65a, 66a that are laid one on the other and brought into contact with each other in the inside of the hermetically sealed container 6 when the front end cover 61 and the trunk cover 62 are connected to each other. In this embodiment, the connection terminal section 65 of the front end cover 61 is located inside relative to the connection terminal section 66 of the trunk cover 62 of the hermetically sealed container 6 and the outer surface thereof operates as the connection surface 65a. In other words, the connection terminal section 66 of the trunk cover 62 is located outside relative to the connection terminal section 65 of the front end cover 61 of the hermetically sealed container 6 and the inner surface thereof operates as the connection surface 66a. The outer diameter of the connection surface 65a is made subsequently equal to the inner diameter of the connection surface 66a. The connection terminal sections 65, 66 are typically so formed that they show a substantially straight profile and the draft angle thereof are 0° relative the respective molds, while the outer diameter of the connection surface 65a is made subsequently equal to the inner diameter of the connection surface 66a so that the two cylindrical sections may be connected to each other with ease.

A projection 65b, or a ridge, is formed peripherally and endlessly on the entire connection surface 65a, while a groove 66b is formed peripherally and endlessly on the entire connection surface 66a. The projection 65b and the groove 66b are brought into engagement with each other when the connection surfaces 65a and 66a are properly laid one on the other. Thus, the projection 65b and the groove 66b operate as connection/engagement means for retaining the connected state of the front end cover 61 and the trunk cover 62 once they are brought into mutual engagement in this way.

As shown in FIGS. 2 through 5, the lighting means 7 has a disk-shaped lighting substrate 71 having a central through hole 71a, six light emitting bodies including five white LEDs 72 and a single ultraviolet LED 95 arranged on the front surface of the lighting substrate 71 (at the side of the front end cover 61 in FIG. 2) and a chip member 74 of the circuits arranged on the rear surface of the lighting substrate 71 (at the side of the image pickup substrate 81 in FIG. 2) to drive the white LEDs 72 and the ultraviolet LED 95. Light emitted from the white LEDs 72 and the ultraviolet LED 95 is directed outwardly toward the front end cover 61.

As shown in FIG. 5, each of the white LEDs 72 and the ultraviolet LED 95 has an electrode section including a pair of electrodes 72a connected to the lighting substrate 71 and an irradiation section 72b formed on an upper part of the electrode section. The irradiation section 72b has longitudinal end facets 72b1 located inside the end facets 72a1 of the electrode section so that they show a step-like profile. As a voltage is applied to the electrodes 72a of each of the white LEDs 72, the irradiation section 72b emits light from the top surface to the outside.

As shown in FIG. 4, the white LEDs 72 are arranged around an imaging lens 83 that is the optical system of the image pickup means 8, which will be described in greater detail hereinafter, on the lighting substrate 71. In other words, the white LEDs 72 are centered at the imaging lens 83 of the image pickup means 8 with their longitudinal directions extending along circle A whose radius is greater than the field of view of the imaging lens 83 that is defined by the optical characteristics of the imaging lens 83.

The ultraviolet LED 95 is a single ultraviolet LED arranged along the circle A with the white LEDs 72 on the lighting substrate 71 as shown in FIG. 5. It is an LED typically of GaN that emit ultraviolet rays showing a peak of spectrum at a short wavelength.

Figure 8:
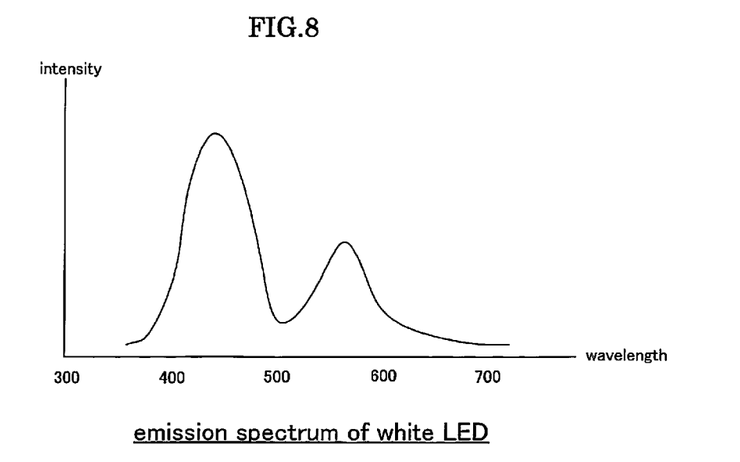
FIG. 8 is a schematic illustration of the emission spectrum of the white LEDs 72.
Figure 9:
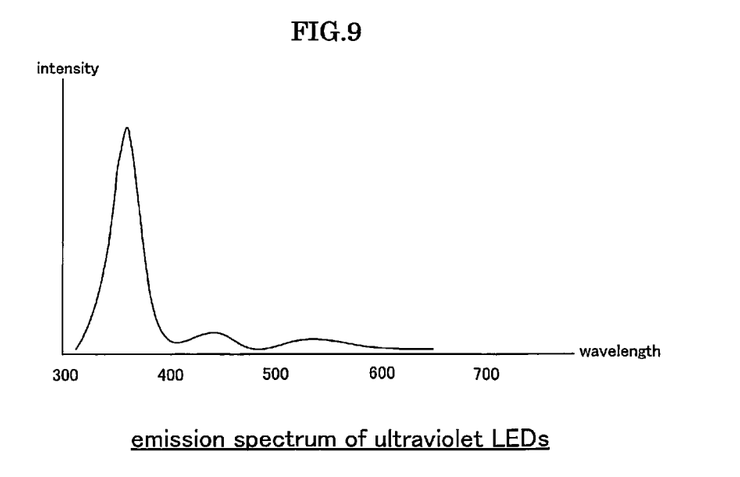
FIG. 9 is a schematic illustration of the emission spectrum of the ultraviolet LED 95.

FIG. 8 is a schematic illustration of the emission spectrum of the white LEDs 72 and FIG. 9 is a schematic illustration of the emission spectrum of the ultraviolet LED 95.

As shown in FIG. 9, the ultraviolet LED 95 is a light emitting device showing a sharp peak of spectrum at a short wavelength of about 380 nm. For the purpose of the present invention, the photocatalytic coating 96 of the front end cover 61 is brought into an excited state by irradiating it with ultraviolet rays by means of the ultraviolet LED 95 to give rise to a hydrophilic effect on the outer surface of the front end cover 61. The lighting of a capsule endoscope according to the present invention does not need to be adjusted for color nor it influence the image obtained by the endoscope when an ultraviolet LED 95 showing a sharp peak of spectrum at a short wavelength is used. Additionally, the above-identified effect can be achieved only by replacing one of the white LEDs that have conventionally been used as light source with an ultraviolet LED 95.

While the ultraviolet LED 95 shows a peak of spectrum at a wavelength of about 380 nm as described above, the excitation peak of the ordinary white LEDs 72 is found at or around 460 nm and one of the opposite ends of the spectrum is at about 380 nm as shown in FIG. 8.

Figure 10A:
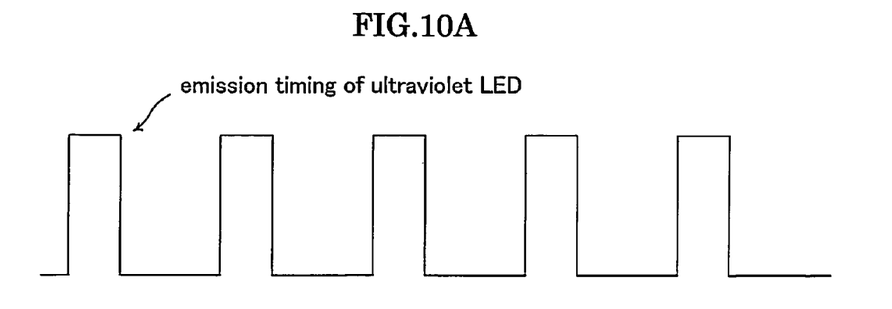
FIGS. 10A, 10B and 10C are timing charts of the emission timings of the ultraviolet LED and the white LEDs and the image pickup timing of the image pickup means.
Figure 10B:
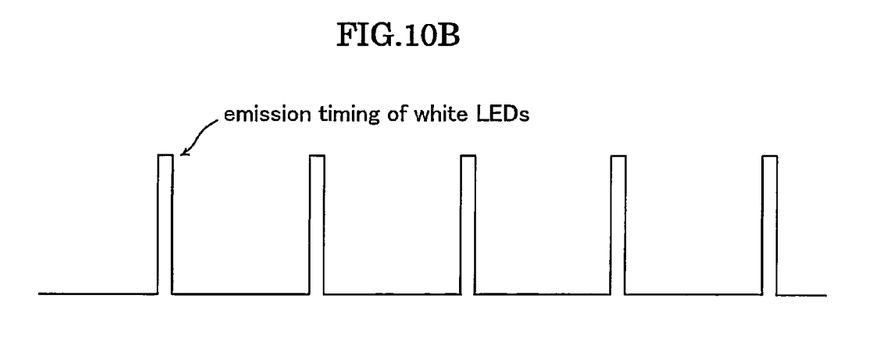
Figure 10C:
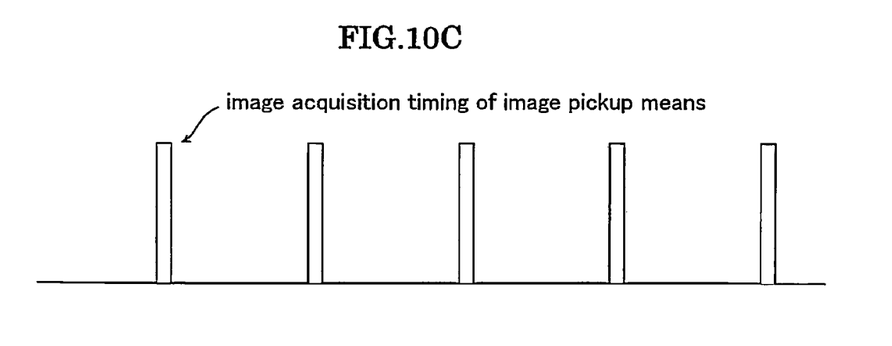

Now, a mode of emission timings of the white LEDs 72 and the ultraviolet LED 95 will be described below. FIGS. 10A, 10B and 10C are timing charts of the emission timings of the ultraviolet LED and the white LEDs and the image pickup timing of the image pickup means.

The image pickup means 8 acquires images at a frequency of two frames per second. The image pickup means 8 receives reflected light produced by irradiation of light by the white LEDs 72 and picks up an image of the site of examination.

Thus, the function execution means controls the timing of the image pickup operation of the image pickup means 8 and that of emission of light of the white LED 72 in an interlocked manner.

The ultraviolet LED 95 brings the photocatalytic coating 96 into an excited state as it irradiates ultraviolet rays and the excited state of the photocatalytic coating 96 lasts for a predetermined time period after the excitation of the photocatalytic coating 96. Therefore, the ultraviolet LED 95 preferably emits ultraviolet rays at a time when the image pickup means 8 is not operating to pick up an image so that the emission of ultraviolet rays may not influence the image pickup operation of the image pickup means 8. More specifically, as shown in FIGS. 10A through 10C, the timing of emission of the ultraviolet LED 95 is preferably oppositely phased to the timing of emission of the white LEDs 72 and the timing of the image pickup operation of the image pickup means 8. Note that the emission timings shown in FIGS. 10A through 10C are only examples and the present invention is by no means limited by such emission timings.

Now, the directivity of emission of light of the white LEDs 72, that of emission of ultraviolet rays of the ultraviolet LED 95 and the angle of the field of view of the image pickup means 8 will be described below by referring to FIG. 7. An angle θ not less than 90° is selected for the field of view of the image pickup means 8 and the range of the front end cover 61 that corresponds to the angle of the field of view of the image pickup means 8 is indicated by α in FIG. 7.

The white LEDs 72 and the ultraviolet LED 95 emit lowly directional rays within an angular range of ø. (While only the angular range of emission of the ultraviolet LED 95 is shown in FIG. 7, the same angular range is also applicable to the white LEDs 72.) The range of emission of ultraviolet rays of the ultraviolet LED 95 is indicated by β in FIG. 7. The range β fully covers the range α that corresponds to the angle of the field of view of the image pickup means 8. Similarly, each of the five white LEDs 72 emits light within an angular range of β, which fully covers the range α that corresponds to the angle of the field of view of the image pickup means 8. Thus, the five white LEDs 72 and the single ultraviolet LED 95 arranged along the circle A can satisfactorily operate as light source for the image pickup operation of the image pickup means 8 and, at the same time, excite the photocatalytic coating 96.

As shown in FIG. 2, the image pickup means 8 includes a disk-shaped image pickup substrate 81, a solid state image sensor 82 such as a CCD or a CMOS arranged in front of the image pickup substrate 81 (at the side of the lighting substrate 71 in -FIG. 2) and an imaging lens 83 for imaging an image of the subject on the solid state image sensor 82. The imaging lens 83 is arranged in front of the solid state image sensor 82 (at the side of the lighting substrate 71 in FIG. 2) and located at the side of the subject. It includes a first lens 83*a* and a second lens 83*b* fitted to a movable frame 84*a*. The movable frame 84*a* constitutes a focus adjustment system 84 with a fixed frame 84*b*. The focus adjustment system 84 drives the first lens 83*a* and the second lens 83*b* to move along the optical axis of the imaging lens 83. The movable frame 84*a* is put into through hole 71*a* of the lighting substrate 71 to direct the optical axis of the imaging lens 83 to the front side of the lighting substrate 71. With this arrangement, the image pickup means 8 can pick up an image of a subject within the area irradiated with light emitted from the lighting means 7. A chip member 85 including a circuit for driving the solid state image sensor 82 is arranged in front of the image pickup substrate 81 so as to surround the solid state image sensor 82.

As shown in FIGS. 2 and 3, the control means 9 includes a DSP (digital signal processor) 91, which is arranged on the rear surface of the image pickup substrate 81 and surrounded by a chip member 92. The DSP 91 takes a key role for driving and controlling the capsule endoscope 3. More specifically, the DSP 91 drives and controls the solid state image sensor 82, processes the output signals of the latter and also drives and controls the lighting means 7. The chip member 92 arranged on the rear surface of the image pickup substrate 81 is a semiconductor member having a function of mixing the two signals of the image signal and the clock signal output from the DSP 91 to form a single signal before being transmitted from the wireless transmission means 20.

As shown in FIG. 2, the power accumulation means 10 includes button-type dry-cell batteries 13 such as silver oxide batteries, a disk-shaped switch substrate 11, a reed switch 14 and a power supply control IC 15 along with a switch section 16 arranged in front of the switch substrate 11 (at the side of the image pickup substrate 81 in FIG. 2) and a power supply section 18. Two or more than two button-type dry-cell batteries 13 are arranged. In this embodiment, two button-type dry-cell batteries 13 are arranged and connected in series with the anode caps directed rearward. Note that the batteries 13 are not limited to silver oxide batteries and may alternatively be rechargeable batteries or generator batteries. The member of batteries is not limited to two. A contact 17 formed by using a leaf spring is arranged on the rear surface of the switch substrate 11. The contact 17 is held in contact with the cathode can of the front side button-type dry-cell battery 13 and urges the button-type dry-cell battery 13 rearwards (at the side of the power supply substrate 12 in FIG. 2) by the urging force of the leaf spring.

The power supply section 18 includes a disk-shaped power supply substrate 12 and a regulator 19 arranged on the rear surface of the power supply substrate 12 (at the side of the rear end section 64 in FIG. 2). The regulator 19 is a controller that typically lowers the voltage obtained by the button-type dry-cell batteries 13 in order to produce a constant voltage that is always necessary for the system. Although not shown in FIG. 2, a contact that is held in contact with the anode cap of the rear side button-type dry-cell battery 13 is arranged on the front surface of the power supply substrate 12 (at the side of the switch substrate 11 in FIG. 2). In this embodiment, the plurality of button-type dry-cell batteries 13 are arranged between the switch substrate 11 and the power supply substrate 12 and connected in series in the power accumulation means 10 to supply power to the function execution means.

The wireless transmission means 20 includes a transmission substrate 21 that is made to show a cylindrical profile and has a internal space region, an oscillation circuit 22 arranged in the inside of the transmission substrate 21, an antenna 23 arranged on the rear surface of the transmission substrate 21 (at the side of the rear end section 64 in FIG. 2) and a connection terminal 24 connected to a flexible substrate 31 typically by means of solder. As shown in FIG. 2, the antenna 23 is coil-shaped and arranged on the rear surface of the transmission substrate 21. The wireless transmission means 20 takes out a signal showing a constant frequency, a constant amplitude and a constant waveform from the signal produced by mixing from the chip member 92 (semiconductor member) by means of the oscillation circuit 22 and transmits it to the outside of the capsule endoscope 3 from the antenna 23.

The lighting substrate 71, the image pickup substrate 81, the switch substrate 11, the power supply substrate 12 and the transmission substrate 21 are rigid substrates. As shown in FIG. 3, these rigid substrates are arranged with a series of flexible substrates 31 interposed among them to produce a rigid-flex wiring board 32. More specifically, the rigid substrates are arranged in the order of the lighting substrate 71, the image pickup substrate 81, the switch substrate 11, the power supply substrate 12 and the transmission substrate 21 at predetermined intervals with the flexible substrates 31 interposed among them and electrically connected to each other. Then, the lighting substrate 71, the image pickup substrate 81, the switch substrate 81, the power supply substrate 12 and the transmission substrate 21 are laid one on the other in the longitudinal direction of the capsule endoscope 3 between the front end cover 61 and the rear end section 64 as the rigid-flex wiring board 32 is folded at the flexible substrates 31.

As the white LEDs 72 showing a step-like profile are centered at the imaging lens 83 of the image pickup means 8 with their longitudinal directions extending along circle A whose radius is greater than the field of view of the imaging lens 83 that is defined by the optical characteristics of the imaging lens 83. The white LEDs are separated from the front end cover by a large distance to allow the capsule endoscope to be downsized and optical flare to be prevented from taking place.

Thus, the capsule endoscope 3 of this embodiment of the present invention provides an advantage that it reduces any food residue and/or mucus that can adhere to the front end cover 61 and prevents any fall of the efficiency of observation from taking place because of the arrangement of the hydrophilic coat. Thus, this embodiment can pick up excellent images in the inside of the body cavity.

Figure 11:
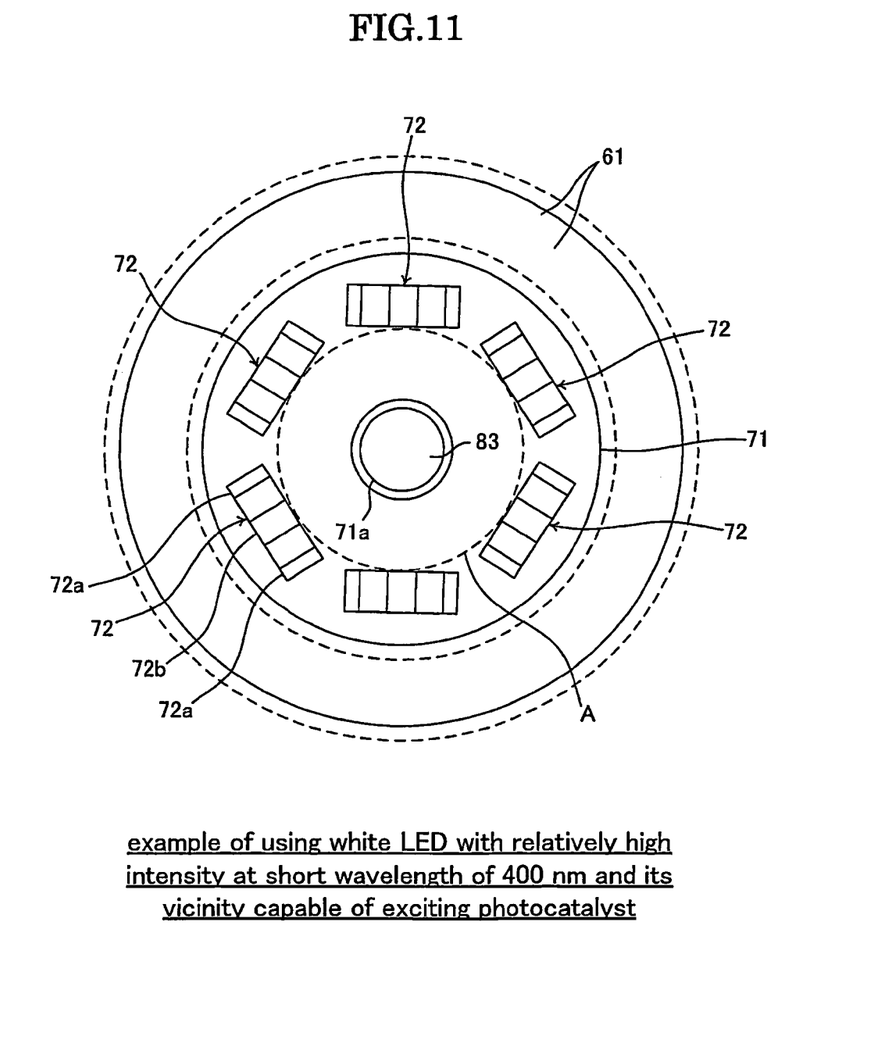
FIG. 11 is a schematic front view of the lighting substrate of another embodiment of capsule endoscope according to the present invention.

Now, another embodiment of the present invention will be described below. FIG. 11 is a schematic front view of the lighting substrate of another embodiment of capsule endoscope according to the present invention. This embodiment differs from the above-described embodiment in that the arrangement of light emitting devices for exciting the photocatalytic coating 96. Otherwise, this embodiment is same as the above-described embodiment. No ultraviolet LED 95 for exclusively exciting the photocatalytic coating 96 is provided in this embodiment but white LEDs 72 for emitting light of a short wavelength of about 400 nm with a relatively high intensity that can excite the photocatalytic coating 96 are employed instead. More specifically, a total of six white LEDs 72 are arranged along circle A in this embodiment. Thus, in addition to the advantage of reducing any food residue and/or mucus that can adhere to the front end cover 61 and preventing any fall of the efficiency of observation from taking place because of the arrangement of the hydrophilic coat of the above described embodiment, this embodiment provides an additional advantage that it does not require a special ultraviolet LED and hence can reduce the manufacturing cost.

Figure 12:
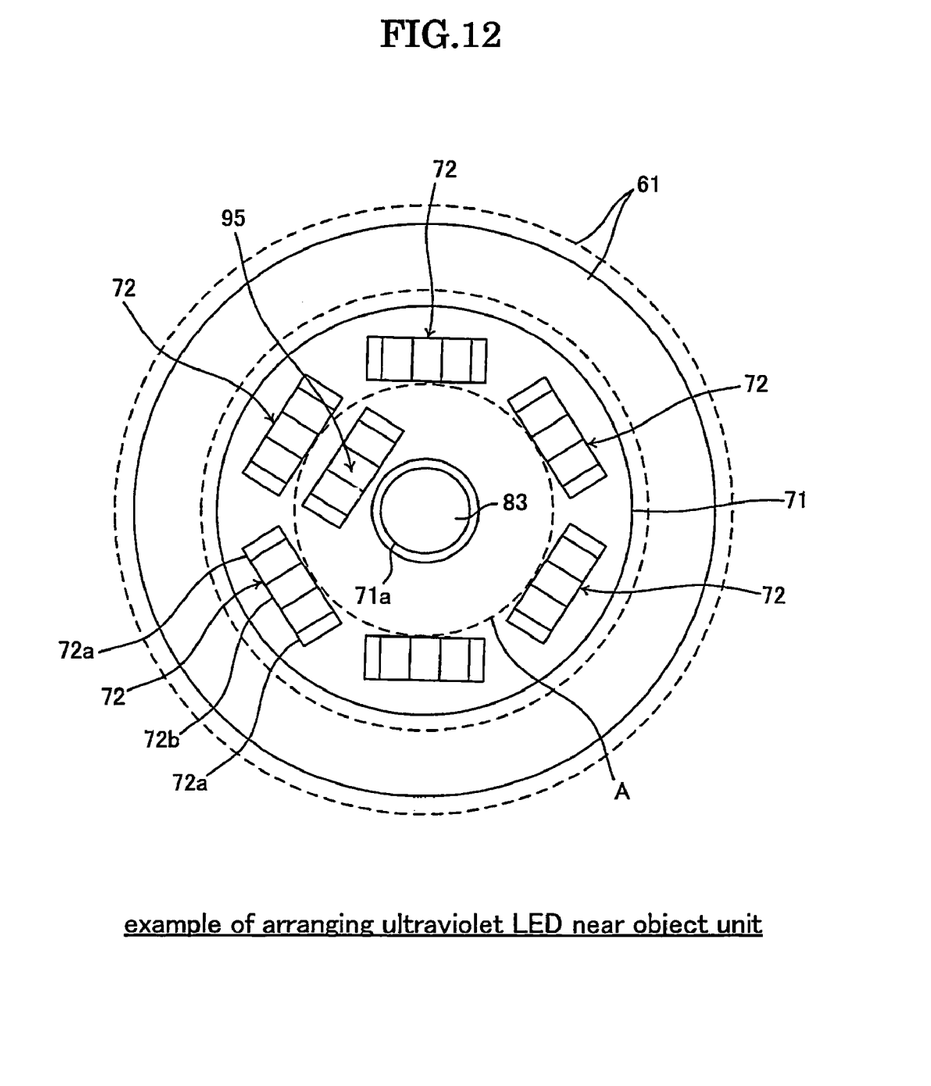
FIG. 12 is a schematic front view of the lighting substrate of still another embodiment of capsule endoscope according to the present invention.

Now, a still another embodiment of the present invention will be described below. FIG. 12 is a schematic front view of the lighting substrate of still another embodiment of capsule endoscope according to the present invention. This embodiment differs from the preceding embodiments in terms of arrangement of light emitting devices. A total of six white LEDs 72 are arranged along circle A and an ultraviolet LED 95 is arranged in the inside of circle A. The subject can be illuminated slightly unevenly when five white LEDs 72 and a single ultraviolet LED 95 are arranged along circle A, in other words, white LEDs 72 are arranged unevenly along circle A as light sources at the time of the image pickup operation of the image pickup means 8, as in the preceding embodiment. However, this embodiment is free from such a problem of an unevenly illuminated subject and hence can pick up excellent images.

Figure 13:
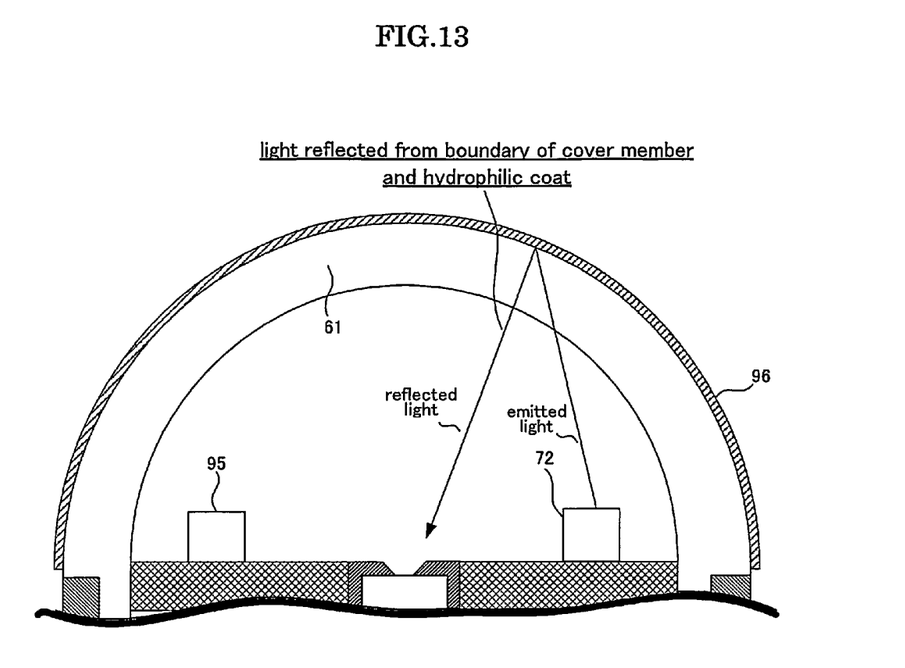
FIG. 13 is a schematic cross-sectional view of the front end cover and its vicinity of any of the preceding embodiments of capsule endoscope according to the present invention.
Figure 14:
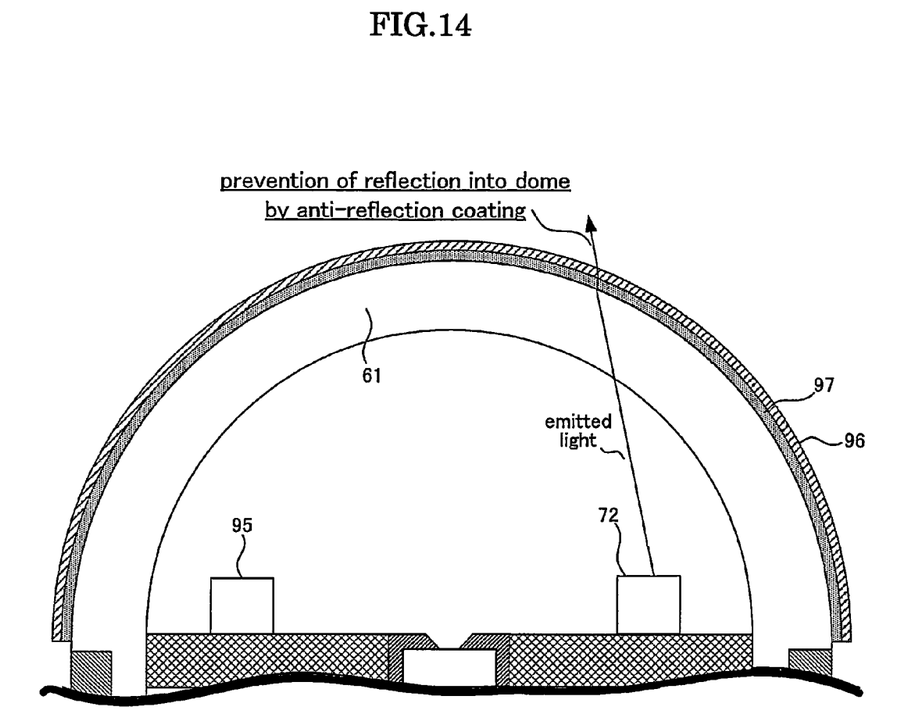
FIG. 14 is a schematic cross-sectional view of the front end cover and its vicinity of still another embodiment of capsule endoscope according to the present invention.

Now, still another embodiment of the present invention will be described below by referring to FIGS. 13 and 14. FIG. 13 is a schematic cross-sectional view of the front end cover and its vicinity of any of the preceding embodiments of capsule endoscope according to the present invention. FIG. 14 is a schematic cross-sectional view of the front end cover and its vicinity of this still another embodiment of capsule endoscope according to the present invention.

As seen from FIG. 13 showing a cross-sectional view of any of the preceding embodiments, as the white LEDs 72 emit light as light sources when an image is picked up by the image pickup means 8, emitted light is reflected by the boundary of the front end cover 61 and the photocatalytic coating 96 and reflected light can enter the image pickup means 8 to affect the image picked up by the image pickup means 8. To avoid this problem, one or more than one thin films 97 typically made of $SiO_2$ that show a refractive index different from the refractive index of the material of the photocatalytic coating 96 are arranged on the front end cover 61 before laying the photocatalytic coating 96 in this embodiment. Thus, reflection of light into the dome by the front end cover 61 is prevented from taking place when an image is picked up by the image pickup means 8 so that no reflected light can enter the image pickup means 8 to affect the image picked up by the image pickup means 8. As a result, this embodiment is free from the problem of reflected light entering the image pickup means 8 and can pick up excellent images.

While the present invention is described above in detail by way of various embodiments, the scope of the present invention includes different combinations of any of the components of the above-described embodiments.

What is claimed is:

1. A capsule endoscope comprising:
   a dome-shaped front end cover provided on the outer surface with a hydrophilic coat;
   image pickup means arranged in the front end cover to pick up images of the inside of an object of examination into which the endoscope is introduced and acquire image information on the inside of the object of examination; and
   a lighting section arranged around the image pickup means within the dome-shaped front end cover;
   wherein the hydrophilic coat is arranged after arranging a layer of coat film of a material having a refractive index different from the refractive index of the material of the hydrophilic coat on the outer surface of the front end cover.

2. The capsule endoscope according to claim 1, wherein the viewing angle of the image pickup means is not less than 90° and the hydrophilic coat is photocatalytic coating.

3. The capsule endoscope according to claim 1, wherein the lighting section is formed by using white LEDs.

4. The capsule endoscope according to claim 1, wherein the lighting section is formed by using white LEDs and an ultraviolet LED.

5. The capsule endoscope according to claim 4, wherein the timing of emission of light of the white LEDs and the timing of emission of light of the ultraviolet LED are differentiated from each other.

6. The capsule endoscope according to claim 1, wherein the hardness of the material of the hydrophilic coat is higher than the hardness of the material of the front end cover.

* * * * *